US007910548B2

(12) United States Patent
Duft et al.

(10) Patent No.: US 7,910,548 B2
(45) Date of Patent: *Mar. 22, 2011

(54) METHODS FOR TREATING OBESITY

(75) Inventors: Bradford J. Duft, Rancho Santa Fe, CA (US); Orville G. Kolterman, Poway, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 1404 days.

This patent is subject to a terminal disclaimer.

(21) Appl. No.: 08/870,762

(22) Filed: Jun. 6, 1997

(65) Prior Publication Data

US 2003/0026812 A1  Feb. 6, 2003

(51) Int. Cl.
*A61K 38/00* (2006.01)
*A61K 39/00* (2006.01)

(52) U.S. Cl. ........ 514/12; 514/909; 424/198.1; 530/300

(58) Field of Classification Search ............... 424/198.1; 514/12, 909, 2, 866
See application file for complete search history.

(56) References Cited

U.S. PATENT DOCUMENTS

| 4,443,619 | A | * | 4/1984 | Guthrie et al. | 549/518 |
|---|---|---|---|---|---|
| 4,960,759 | A | * | 10/1990 | De Luca et al. | 514/50 |
| 5,124,314 | A | * | 6/1992 | Cooper | 514/4 |
| 5,134,164 | A | * | 7/1992 | Meglasson | 514/565 |
| 5,175,145 | A | | 12/1992 | Cooper | |
| 5,187,154 | A | * | 2/1993 | Phillips et al. | 514/12 |
| 5,234,906 | A | | 8/1993 | Young et al. | |
| 5,264,372 | A | | 11/1993 | Beaumont et al. | |
| 5,266,561 | A | | 11/1993 | Cooper et al. | |
| 5,280,014 | A | * | 1/1994 | Cooper et al. | 514/12 |
| 5,321,008 | A | * | 6/1994 | Beaumont et al. | 514/4 |
| 5,364,841 | A | | 11/1994 | Cooper et al. | |
| 5,367,052 | A | | 11/1994 | Cooper et al. | |
| 5,376,638 | A | | 12/1994 | Young et al. | |
| 5,462,742 | A | * | 10/1995 | Bogentoft et al. | 424/439 |
| 5,498,424 | A | * | 3/1996 | Klein et al. | 424/464 |
| 5,527,788 | A | * | 6/1996 | Svec et al. | 514/169 |
| 5,578,579 | A | * | 11/1996 | Lartey et al. | 514/29 |
| 5,656,590 | A | | 8/1997 | Rink et al. | |
| 5,686,411 | A | * | 11/1997 | Gaeta et al. | 514/12 |
| 5,690,691 | A | * | 11/1997 | Chen et al. | 607/40 |
| 5,739,106 | A | * | 4/1998 | Rink et al. | 514/12 |
| 5,739,129 | A | * | 4/1998 | Aquino et al. | 514/221 |
| 5,830,434 | A | * | 11/1998 | Taylor et al. | 424/9.2 |
| 5,877,283 | A | * | 3/1999 | Shuldiner et al. | 530/350 |
| 5,900,435 | A | * | 5/1999 | Meglasson | 514/565 |
| 5,932,779 | A | * | 8/1999 | Lee et al. | 800/2 |
| 5,955,443 | A | * | 9/1999 | Bennette et al. | 514/44 |
| 5,972,621 | A | * | 10/1999 | Tartaglia et al. | 435/7.1 |
| 6,008,242 | A | * | 12/1999 | Korsgaard et al. | 514/422 |
| 6,020,361 | A | * | 2/2000 | Venkatesan | 514/452 |
| 6,043,346 | A | * | 3/2000 | Kleyn et al. | 530/387.9 |
| 6,100,047 | A | * | 8/2000 | Wilkison et al. | 435/7.2 |
| 6,110,707 | A | * | 8/2000 | Newgard et al. | 435/69.4 |
| 6,114,304 | A | * | 9/2000 | Kolterman et al. | 514/12 |
| 6,187,991 | B1 | * | 2/2001 | Soeller et al. | 800/2 |
| 6,956,026 | B2 | * | 10/2005 | Beeley et al. | 514/12 |
| 2005/0197287 | A1 | * | 9/2005 | Mack et al. | 514/12 |

FOREIGN PATENT DOCUMENTS

| EP | 0408294 | * | 7/1990 |
|---|---|---|---|
| WO | WO 91/16917 | * | 11/1991 |
| WO | WO 92/15317 | | 9/1992 |
| WO | 9220367 | | 11/1992 |
| WO | WO/9310146 | | 5/1993 |
| WO | WO 94/26292 | * | 11/1994 |
| WO | WO 95/07098 | * | 3/1995 |
| WO | WO 95/28419 | * | 10/1995 |
| WO | WO 96/37612 | * | 11/1996 |
| WO | WO 96/40220 | * | 12/1996 |
| WO | WO/9640196 | | 12/1996 |

OTHER PUBLICATIONS

Kolterman et al. (I) Diabetologia 39: 492-496, Apr. 1996.*
Moyses et al. Diabetic Med. 13 (suppl. 1): 34-38, Sep. 1996.*
Thompson et al. Diabetes 46: 632-636, Apr. 1997.*
Cooper et al. Biochim. Biophys. Acta 1014(3): 247-258, Abstract, 1989.*
Weisser et al. J. Clin. Pharmacol. 37(6): 453-473, Jun. 1997.*
Morley et al. Am. J. Physiol. 267: R178-R184, 1994.*
Morley et al. Can. J. Physiol. Pharmacol. 73: 104-1046, 1995.*
Lutz et al. (Physiol. & Behavior 55(5): 891-895, abstract, 1994.*
Kolterman, Diabetic Med. 14 (suppl. 1): s35-s38, Jun. 1997.*
Exp. Opin. Ther. Patents 4(11): 1383-1384, 1994.*
Koopman et al. Neth. J. Med. 41 (1-2): 82-90, 1992.*
Ludwik, Wien Klin. Wochenster 109 (11): 379-383, Jun. 6, 1997, abstract.*
Rowland et al. CNS Drugs, Jun. 1997, 7(6): 419-426.*
Porte, Diabetes, 40( ): 166-180, 1991.*
Young et al. Drug Dev. Res. 37: 231-48, 1996.*
Janes et al. Diabetes, 45 (suppl. 2): A 865, p. 235A, 1996.*
Colburn et al. J. Clin. Pharmacol. 36: 13-24, 1996.*
Thompson et al. Abstract Book, 55th Annual Meeting and Scientific Sessions, Jun. 10-13, 1995, Georgia World Congress Center, Atlanta, Georgia. Diabetes 44: suppl. 1, Ab. 469, p. 127A, 1995.*
Morley et al. Peptides 12: 865-869, 1991.*
Lutz et al. Br. Vet. J. 149 (6): 527-536, Nov.-Dec. 1993, abstract.*
Thomas et al. Circulation 91: 764-770, abstract, 1995.*
Johnston et al. J. Hypertension 10: 393-397, abstract, 1992.*
Scheen et al. Drugs 54: 355-368, Sep. 1997, abstract.*
Stogdale et al. Cornell Vet. 76: 156-174, abstract, 1986.*
Griver et al. Nutrition Res. 14: 465-483, abstract, 1994.*
Arnelo et al. Am. J. Physiol. 271: 6 Pt 2: R1654-R1659, Dec. 1996.*
Arnelo et al. Scand. J. Gastroenterol. 31: 83-89 Jan. 1996.*
Wang et al. Diabetes 42 (2): 330-335, 1993, abstract.*
Weintraub et al. Nutrition Rev. 49: 237-249, 1989.*
Thompson et al. Diabetes 48: Suppl. 1, p. 30A, 0116, May 2, 1997.*
The Random House Dictionary, (Ed) Flexner et al., Random House, p. 32, New York, 1984.*
Frishman et al. In: Cardiovascular Pharmacotherapeutics. (Eds) Frishman WH et al. McGraw-Hill Health Professions Division, New York, Chapter 48, pp. 1093-1114, Feb. 1997.*
Kong et al. Diabetologia 40: 82-88, Jan. 1997.*

(Continued)

*Primary Examiner* — S. Devi

(57) ABSTRACT

Methods for treating obesity are disclosed which comprise administration of a therapeutically effective amount of an amylin or an amylin agonist alone or in conjunction with another obesity relief agent.

10 Claims, No Drawings

OTHER PUBLICATIONS

Jonderko et al. Aliment. Pharmacol. Ther. 5: 413-418, 1991.*
Morley et al. Pharmcol. Biochem. Behav. 44: 577-580, 1993.*
Jonderko et al. Israel J. Med. Sci. 25: 20-24, 1989.*
Frank et al. Gastroenterology 109: 755-785, 1995.*
Balasubramaniam et al. Peptides 12: 919-924, 1991.*
Kong et al. Diabetes 46: Suppl. 1, 154A, 1997.*
Clementi et al. Experientia 52: 677-679, 1996.*
Brown et al. Diabetes 43: Suppl. 1: 172A, 1994.*
Wright et al. Gastroenterology 84: 747-751, 1986.*
Edwards et al. Life Sci. 51: 1819-1912, 1992.*
Kolterman et al. Diabetologia 37: Suppl. 1: A72, 278, 1994.*
Young et al. Diabetes 45: Suppl. 2, p. 187A, A689, 1996.*
Tsanev. Vutr. Boles 23: 12-17, 1984, abstract.*
Szabo et al. Vnitr Lek. 44: 145-150, Mar. 1998.*
Kosmiski et al. Curr. Opin. Endocrin. Diabet. 4: 36-39, 1997.*
Baron et al. Current Drug Targets—Immune, Endocrine & Metabolic Disorders 2: 63-82, 2002.*
Ratner et al. Diabetes Technol. Ther. 4: 51-61, 2002.*
Hollander et al. Obesity Res. 12: 661-668, Apr. 2004.*
Kopelman Editotial. Internat. J. Obesity 23: Suppl. 7, S1, 1999.*
Itasaka et al. Psychiatr. Clin. Neurosci. 54: 340-341, Jun. 2000, abstract.*
Pi-Sunyer. Diabetes Care 28: 1526-1527, 2005.*
Olefsky JM. In: Harrison's Principles of Internal Medicine, 12th Edition, McGraw-Hill Book Company, pp. 411-416, 1961.*
Kolterman et al., "Reduction of postprandial hyperglycemia in subjects with IDDM by intravenous infusion of AC137, a human amylin analogue," *Diabetes Care* 18(8):(Abstract) (1995).
Kong et al., "Infusion of pramlintide, a human amylin analogue, delays gastric emptying in men with IDDM," *Diabetologia* 40(1):82-88 (1997).
Kong et al., "The effect of single doses of pramlintide on gastric emptying of two meals in men with IDDM," *Diabetologia* 41(5):577-583 (1998).
Nyholm et al., "Acute effects of the human amylin analog AC137 on basal and insulin-stimulated eugycemic and hypoglycemic fuel matabolism in patients with insulin-dependent diabetes mellitus," *J. Clin. Endocrinol. Metab.* 81(3):1083-1089 (1996).
Schmitz et al., "Effects of amylin and the amylin agonist pramlintide on glucose metabolism," *Diabetic Med.* 14(2):S19-S23 (1997).
Thompson et al., "Effects of 4 weeks' administration of pramlintide, a human amylin analogue, on glycaemia control in patients with IDDM: effects on plasma glucose profiles and serum fructosamine concentrations," *Diabetologia* 40(11):1278-1285 (1997).
Thompson et al., "Pramlintide: A human amylin analogue reduced postprandial plasma glucose, insulin, and C-peptide concentrations in patients with type 2 diabetes," Diabetic Med. 14(7):547-555 (1997).
Alam et al., "Selective Antagonism of Calcitonin-Induced Osteoclastic Quiescence (Q Effect) by Human Calcitonin Gene-Related Peptide-(Val$^8$Phe$^{37}$), " *Biochem. Biophys. Res. Commun.*, 179(1):134-139 (1991).
Beaumont et al., "Regulation of Muscle Glycogen Metabolism by CGRP and Amylin: CGRP Receptors Not Involved," *Br. J. Pharmacol.*, 115(5):713-715 (1995).
Brain et al., "Amylin Amide, Which Is Structurally Similar to Calcitonin Gene-Related Peptide (CGRP), Stimulates Increased Blood Flow In Vivo," *Eur. J. Pharmacol.*, 183:2221 (1990).
Bray, G.A., "Drug Treatment of Obesity," *Am. J. Clin. Nutr.*, 55:538S-544S (1992).
Bray, G.A. "Treatment for Obesity: A Nutrient Balance/Nutrient Partition Approach," *Nutrition Reviews*, 49:33-45 (1991).
Broderick et al., "Human and Rat Amylin Have No Effects on Insulin Secretion in Isolated Rat Pancreatic Islets," *Biochem. Biophys. Res. Commun.*, 177(3):932-938 (1991).
Chance et al., "Anorexia Following the Intrahypothalamc Administration of Amylin," *Brain Res.*, 539:352-354 (1991).
Chance et al., "Anorexia Following the Systemic Injection of Amylin," *Brain Res.*, 607:185-188 (1993).

Chantry et al., "Cross-Reactivity of Amylin with Calcitonin-Gene-Related Peptide Binding Sites in Rat Liver and Skeletal Muscle Membranes," *Biochem. J.*, 277:139-143 (1991).
Cooper et al., "The Amylin Superfamily: A Novel Grouping of Biologically Active Polypeptides Related to the Insulin A-Chain," *Prog. Growth Factor Research*, 1:99-105 (1989).
Cooper et al., "Amylin Found in Amyloid Deposits in Human Type 2 Diabetes Mellitus May Be a Hormone that Regulates Glycogen Metabolism in Skeletal Muscle," *Proc. Nat'l. Acad. Sci. USA*, 85:7763-7766 (1988).
Cooper et al., "Purification and Characterization of a Peptide from. Axnyloid-Rich Pancreases of Type 2 Diabetic Patients,", *Proc. Nat'l. Acad. Sci. USA*, 84:8628-8632 (1987).
Deems et al., "Amylin or CGRP (8-37) Fragments Reverse Amylin-Induced Inhibition of $^{14}$C-Glycogen Accumulation," *Biochem. Biophys. Res. Commun.*, 181(1):116-120 (1991).
Follett et al., "Effect of Amylin on Insulin Receptor Kinase Activity In Vivo in the Rat," *Clin. Res.*, 39(1):39A (1991).
Gaeta et al., "Amylin: A New Hormone as a Therapeutic Target in Diabetes Mellitus and Other Metabolic Diseases," *Med. Chem. Res.*, 3:483-490 (1994).
Galeazza et al., "Islet Amyloid Peptide (IAPP) Competes for Two Binding Sites Of CGRP," *Peptides*, 12:585-591 (1991).
Gardiner et al., "Antagonistic Effect of Human α-Calcitonin Gene-Related Peptide (8-37) on Regional Hemodynamic Actions of Rat Islet Amyloid Polypeptide in Conscious Long-Evans Rats," *Diabetes*, 40:948-951 (1991).
Gedulin et al., "Amylin Secretion from the Perfused Pancreas: Dissociation from Insulin and Abnormal Elevation in Insulin-Resistant Diabetic Rats," *Biochem. Biophys. Res. Commun.*, 180(1):782-789 (1991).
Gedulin et al., "Endogenous Amylin and Gastric Emptying in Rats: Comparison with GLP-1 and CCK-8," *Diabetologia*, 38 (Supp. 1):A244 (1995).
Gomez-Foix et al., "Anti-Insulin Effects of Amylin and Calcitonin-Gene-Related Peptide on Hepatic Glycogen Metabolism," *Biochem J.*, 276:607-610 (1991).
Huang et al., "Hyperamylinemia, Hyperinsulinemia, and Insulin Resistance in Genetically Obese LA/N-c*p* Rats," *Hypertension*, 19:I-101-I-109 (1991).
Jung et al., "The Management of Obesity," *Clinical Endocrinology*, 35:11-20 (1991).
Koda et al., "Amylin Concentrations and Glucose Control," *The Lancet*, 339:1179-1180.
Koopmans et al., "Amylin-Induced In Vivo Insulin Resistance in Conscious Rats: The Liver Is More Sensitive To Amylin Than Peripheral Tissues," *Diabetologia*, 34:218-224 (1991).
Leighton et al., "Pancreatic Amylin and Calcitonin Gene-Related Peptide Cause Resistance to Insulin in Skeletal Muscle In Vitro," *Nature*, 335(6191):632-635 (1988).
Ludvik et al., "Amylin: History and Overview," *Diabet. Med.*, 14:S9-S13 (1997).
Lupien et al., "No Measurable Effect of Amylin on Lipolysis in Either White or Brown Isolated Adipocytes from Rats," *Diab. Nutr. Metab.*, 6(1):13-18 (1993).
MacDonald et al., "Infusion of the Human Amylin Analogue, AC137 Delays Gastric Emptying in Men with IDDM," *Diabetologia*, 38(Suppl 1):Abstract.118 (1995).
Molina et al., "Induction of Insulin Resistance In Vivo by Amylin and Calcitonin Gene-Related Peptide," *Diabetes*, 39:260-265 (1990).
Moore et al., "Co-Secretion of Amylin and Insulin from Cultured Islet β-Cells: Modulation by Nutrient Secretagogues, Islet Hormones and Hypoglycemic Agents," *Biochem. Biophys. Res. Commun.*, 179(1):1-9 (1991).
Nowak et al., "Accelerated Gastric Emptying in Diabetic Rodents: Effect of Insulin Treatment and Pancreas Transplantation," *J. Lab. Clin. Med.*, 123(1):110-6 (1994).
Pittner et al., "Amylin and Epinephrine Have No Direct Effect on Glucose Transport in Isolated Rat Soleus Muscle," *FEBS Letts.*, 365(1):98-100 (1995).
Pittner et al., "Molecular Physiology of Amylin," *J. Cell. Biochem.*, 55S:19-28 (1994).

Plourde et al., "CGRP 8-27 Blocks the Inhibition of Gastric Emptying Induced by Intravenous Injection of α-CGRP in Rats," *Life Sci.*, 52:857-862 (1993).

Rink et al., "Structure and Biology of Amylin," *TiPS*, 14:113-118 (1993).

Roden et al., "Effect of Islet Amyloid Polypeptide on Hepatic Insulin Resistance and Glucose Production in the Isolated Perfused Rat Liver," *Diabetologia*, 35:116-120 (1992).

Rosenbloom et al., "Chronic Overtreatment with Insulin in Children and Adolescents," *Am. J. Dis. Child.*, 131(8):881-5 (1977).

Shulutko (Ed.), *Physician's Handbook*, St. Petersburg, p. 496 (1996).

Stephens et al., "Presence of Liver CGRP/Amylin Receptors in Only Nonparenchymal Cells and Absence of Direct Regulation of Rat Liver Glucose Metabolism by CGRP/Amylin," *Diabetes*, 40:395-400 (1991).

Starkova (Ed.), *Clinical Endocrinology*, Moscow, Meditsina, p. 197 (1991).

Wang et al., "$^{8-37}$h-CGRP Antagonizes Actions of Amylin on Carbohydrate Metabolism In Vitro And In Vivo," *FEBS Letts.*, 291(2):195-198 (1991).

Young et al., "Amylin and Insulin in Rat Soleus Muscle: Dose Responses for Cosecreted Noncompetitive Antagonists," *Am. J. Phys.*, 263(2):E274-E281 (1992).

Young et al., "Effects of Amylin on Glucose Metabolism and Glycogenolysis In Vivo and In Vitro," *Am. J. Physiol.*, 259:E457-E461 (1990).

Young et al., "Gastric Emptying Is Accelerated in Diabetic BB Rats and Is Slowed by Subcutaneous Injections of Amylin," *Diabetologia*, 38(6):642-648 (1995).

Young et al., "Amylin Activates-Glycogen Phosphorylase in the Isolated Soleus Muscle of the Rat," *FEBS Letts.*, 281(1,2)149-151 (1991).

Young et al., "$^{8-37}$hCGRP, an Amylin Receptor Antagonist Enhances the Insulin Response and Perturbs the Glucose Response to Infused Arginine in Anesthetized Rats," *Mol. Cell Endocrino.*, 84:R1-R5 (1992).

Zaidi et al, "Amylin in Bone Conservation: Current Evidence and Hypothetical Considerations," *TEM*, 4(8):255-259 (1993).

Zhu et al., "Amylin Increases Cyclic Amp Formation in L6 Myocytes through Calcitonin Gene-Related Peptide Receptors," *Biochem. Biophys. Res. Commun.*, 177(2):771-776 (1991).

Bowie, et al, "Deciphering the MEssage in Protein Sequences: Tolerance to Amino Acid Substitutions", Science, 247:1306-1310, 1990.

Burgess, et al, "Possible Dissociation of the Heparin-binding and Mitogenic Activities of Heparin-binding . . . " J. Cell. Biol., 111:2129-2138, 1990.

Cooper, et al, "Amylin and the Amylin Gene: Structure, Function and Relationship to Islet Amyloid and to Diabetes Mellitus", Biochim. Biophys. Acta, 1014: 247-258, 1989.

Lazar, et al, "Transforming Growth Factor Alpha: Mutation of Aspartic Acid 47 and Leucine 48 Results in Different Biological Activities", Mol. Cellular Biol, 8:1247-1252, 1988.

Scherbaum, W.A., "the Role of Amylin in the Physiology of Glycemic Control", Exp. Clin. Endocrinol. Diabetes, 106:97-102, 1998.

A.A. Young, et al, "Dose Responses for the Slowing of Gastric Emptying in a Rodent Model . . . ", Metabolism, 45: 1-3, Jan. 1996.

Young, et al, "Roles of Amylin in Diabetes and in Regulation of Nutrient Load", Nutrition 14: 524-527, Jun. 1998.

Aronne et al., Obesity, 14(9 Suppl.):A17, Abstract 53-OR (2006).

Aronne et al., J. Clin. Endocrinol. & Metabolism, 92(8):2977-2983 (2007).

Smith et al., Diabetes, 56(Suppl1):A88, Abstract 335-OR (2007).

Smith et al., Am. J. Physiol. Endocrinol. Metab., 293:E620-E627 (2007).

Lotter, et al., "Injections of insulin and changes of body weight", Physiol. Behav., vol. 18, pp. 293-297., 1995.

Lutz, et al., "Amylin decreases meal size in rats", Physiology & Behavior, 1995, 58 (6), pp. 1197-1202.

Morey, et al., "Amylin and food intake in mice: effects on motivation to eat and mechanism of action", Pharmacol. Biochem. Behav., Jan. 1997, 56 (1); pp. 123-129.

\* cited by examiner

METHODS FOR TREATING OBESITY

FIELD OF THE INVENTION

The present invention relates to methods for treating obesity. More particularly, the invention relates to the use of an amylin or agonist of amylin in the treatment of obesity.

INCORPORATION-BY-REFERENCE OF MATERIAL SUBMITTED ON COMPACT DISCS

The sequence listing in the present application is being submitted on two compact discs labeled "Sequence Listing-Copy 1" and "Sequence Listing-Copy 2"; each containing a file of 16 KB in size named "226-104 US SEQ LIST" created on Sep. 29, 2005, the contents of which are hereby incorporated by reference.

BACKGROUND

Amylin

The structure and biology of amylin have previously been reviewed. See, for example, Rink et al., *Trends in Pharmaceutical Sciences*, 14:113-118 (1993); Gaeta and Rink, *Med. Chem. Res.*, 3:483-490 (1994); and, Pittner et al., *J. Cell. Biochem.*, 55S:19-28 (1994). Amylin is a 37 amino acid protein hormone. It was isolated, purified and chemically characterized as the major component of amyloid deposits in the islets of pancreases of deceased human Type 2 diabetics (Cooper et al., *Proc. Natl. Acad. Sci. USA*, 84:8628-8632 (1987)). The amylin molecule has two important post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the C-terminal position, a typical sequence for amidation by protein amidating enzyme, PAM (Cooper et al., *Biochem. Biophys. Acta*, 1014:247-258 (1989)). Amylin is the subject of U.S. Pat. No. 5,367,052, issued Nov. 22, 1995.

In Type 1 diabetes, amylin has been shown to be deficient and combined replacement with insulin has been proposed as a preferred treatment over insulin alone in all forms of diabetes. The use of amylin and other amylin agonists for the treatment of diabetes mellitus is the subject of U.S. Pat. No. 5,175,145, issued Dec. 29, 1992. Pharmaceutical compositions containing amylin and amylin plus insulin are described in U.S. Pat. No. 5,124,314, issued Jun. 23, 1992.

Excess amylin action has been said to mimic key features of Type 2 diabetes and amylin blockade has been proposed as a novel therapeutic strategy. It has been disclosed in U.S. Pat. No. 5,266,561, issued Nov. 30, 1993, that amylin causes reduction in both basal and insulin-stimulated incorporation of labeled glucose into glycogen in skeletal muscle. The latter effect was also disclosed to be shared by calcitonin gene related peptide (CGRP) (see also Leighton and Cooper, *Nature*, 335:632-635 (1988)). Amylin and CGRP were approximately equipotent, showing marked activity at 1 to 10 nM. Amylin is also reported to reduce insulin-stimulated uptake of glucose into skeletal muscle and reduce glycogen content (Young et al., *Amer. J. Physiol.*, 259:45746-1 (1990)). The treatment of Type 2 diabetes and insulin resistance with amylin antagonists is disclosed.

The chemical structure of amylin is nearly 50% identical to the CGRPs, also 37 amino acid proteins which are widespread neurotransmitters with many potent-biological actions, including vasodilation. Amylin and CGRP share the $^2$Cys-$^7$Cys disulphide bridge and the C-terminal amide, both of which are essential for full biologic activity (Cooper et al., *Proc. Natl. Acad. Sci. USA*, 857763-7766 (1988)). Amylin reportedly may be one member of a family of related peptides which includes CGRP, insulin, insulin-like growth factors and the relaxins and which share common genetic heritage (Cooper et al., *Prog. Growth Factor Research*, 1:99-105 (1989)).

Amylin is primarily synthesized in pancreatic beta cells and is secreted in response to nutrient stimuli such as glucose and arginine. Studies with cloned beta-cell tumor lines (Moore et al., *Biochem. Biophys. Res. Commun.*, 179(1) (1991)), isolated islets (Kanatsuka et al., *FEBS Letts.*, 259(1), 199-201 (1989)) and perfused rat pancreases (Ogawa et al., *J. Clin. Invest.*, 85:973-976 (1990)) have shown that short pulses, 10 to 20 minutes, of nutrient secretagogues such as glucose and arginine, stimulate release of amylin as well as insulin. The molar amylin:insulin ratio of the secreted proteins varies between preparations from about 0.01 to 0.4, but appears not to vary much with acute stimuli in any one preparation. However, during prolonged stimulation by elevated glucose, the amylin:insulin ratio can progressively increase (Gedulin et al., *Biochem. Biophys. Res. Commun.*, 180(1): 782-789 (1991)). Thus, amylin and insulin are not always secreted in a constant ratio.

It has been discovered and reported that certain actions of amylin are similar to non-metabolic actions of CGRP and calcitonin; however, the metabolic actions of amylin discovered during investigations of this newly identified protein appear to reflect its primary biologic role. At least some of these metabolic actions are mimicked by CGRP, albeit at doses which are markedly vasodilatory (see, Leighton et al., *Nature*, 335:632-635 (1988); Molina et al., *Diabetes*, 39:260-265 (1990)).

The first discovered action of amylin was the reduction of insulin-stimulated incorporation of glucose into glycogen in rat skeletal muscle (Leighton et al., *Nature*, 335:632-635 (1988)); the muscle was made "insulin-resistant." Subsequent work with rat soleus muscle ex-vivo and in vitro has indicated that amylin reduces glycogen synthase activity, promotes conversion of glycogen phosphorylase from the inactive b form to the active a form, promotes net loss of glycogen (in the presence or absence of insulin), increases glucose-6-phosphate levels, and can increase lactate output (see, e.g., Deems et al., *Biochem. Biophys. Res. Commun.*, 181(1):116-120 (1991)); Young at al., *FEBS Letts*, 281(1,2):149-151 (1991)). Amylin appears not to affect glucose transport per se (e.g., Pittner et al., *FEBS Letts.*, 365(1):98-100 (1995)). Studies of amylin and insulin dose-response relations show that amylin acts as a noncompetitive or functional antagonist of insulin in skeletal muscle (Young et al., *Am. J. Physiol.*, 263(2):E274-E281 (1992)). There is no evidence that amylin interferes with insulin binding to its receptors, or the subsequent activation of insulin receptor tyrosine kinase (Follett et al., *Clinical Research*, 39(1):39A (1991)); Koopmans et al., *Diabetologia*, 34:218-224 (1991)).

It is believed that amylin acts through receptors present in plasma membranes. Studies of amylin and CGRP, and the effect of selective antagonists, suggest that amylin acts via its own receptor (Beaumont et al., *Br. J. Pharmacol.*, 115(5): 713-715 (1995); Wang et al., *FEBS Letts.*, 219:195-198 (1991 b)), counter to the conclusion of other workers that amylin may act primarily at CGRP receptors (e.g., Chantry et al., Biochem. J., 277:139-143 (1991)); Galeazza et al., *Peptides*, 12:585-591 (1991)); Zhu et al., *Biochem. Biophys. Res. Commun.*, 177(2):771-776 (1991)). Amylin receptors and their use in methods for screening and assaying for amylin agonist and antagonist compounds are described in U.S. Pat. No. 5,264,372, issued Nov. 23, 1993.

While amylin has marked effects on hepatic fuel metabolism in vivo, there is no general agreement as to what amylin actions are seen in isolated hepatocytes or perfused liver. The available data do not support the idea that amylin promotes hepatic glycogenolysis, i.e., it does not act like glucagon (e.g., Stephens et al., *Diabetes*, 40:395-400 (1991); Gomez-Foix et al., *Biochem J.*, 276:607-610 (1991)). It has been suggested that amylin may act on the liver to promote conversion of lactate to glycogen and to enhance the amount of glucose able to be liberated by glucagon (see Roden et al., *Diabetologia*, 35:116-120 (1992)). In this way, amylin could act as an anabolic partner to insulin in liver, in contrast to its catabolic action in muscle.

In fat cells, contrary to its action in muscle, amylin has no detectable actions on insulin-stimulated glucose uptake, incorporation of glucose into triglyceride, $CO_2$ production (Cooper et al., *Proc. Natl. Acad. Sci.*, 85:7763-7766 (1988)) epinephrine-stimulated lipolysis, or insulin-inhibition of lipolysis (Lupien and Young, "Diabetes Nutrition and Metabolism—Clinical and Experimental," Vol. 6(1), pages 1318 (February 1993)). Amylin thus exerts tissue-specific effects, with direct action on skeletal muscle, marked indirect (via supply of substrate) and perhaps direct effects on liver, while adipocytes appear "blind" to the presence or absence of amylin.

It has also been reported that amylin can have marked effects on secretion of insulin. In isolated islets (Ohsawa et al., *Biochem. Biophys. Res. Commun.*, 160(2):961-967 (1989)), in the perfused pancreas (Silvestre et al., *Reg. Pept.*, 31:23-31 (1991)), and in the intact rat (Young et al., *Mol. Cell. Endocrinol.*, 84:R1-R5 (1992)), some experiments indicate that amylin inhibits insulin secretion. Other workers, however, have been unable to detect effects of amylin on isolated β-cells, on isolated islets, or in the whole animal (see Broderick et al., *Biochem. Biophys. Res. Commun.*, 177:932-938 (1991) and references therein).

Amylin or amylin agonists potently inhibit gastric emptying in rats (Young et al., *Diabetologia* 38(6):642-648 (1995)), dogs (Brown et al., *Diabetes* 43(Suppl 1):172A (1994)) and humans (Macdonald et al., *Diabetologia* 38(Suppl 1):A32 (abstract 118) (1995)). Gastric emptying is reportedly accelerated in amylin-deficient type 1 diabetic BB rats (Young et al., *Diabetologia*, supra; Nowak et al., *J. Lab. Clin. Med.*, 123(1):110-6 (1994)) and in rats treated with the selective amylin antagonist, AC187 (Gedulin et al., *Diabetologia*, 38(Suppl 1):A244 (1995). The effect of amylin on gastric emptying appears to be physiological (operative at concentrations that normally circulate).

Non-metabolic actions of amylin include vasodilator effects which may be mediated by interaction with CGRP vascular receptors. Reported in vivo tests suggest that amylin is at least about 100 to 1000 times less potent than CGRP as a vasodilator (Brain et al., *Eur. J. Pharmacol.*, 183:2221 (1990); Wang et al., *FEBS Letts.*, 291:195-198 (1991)). The effect of amylin on regional hemodynamic actions, including renal blood flow, in conscious rats has been reported (Gardiner et al., *Diabetes*, 40:948-951 (1991)). The authors noted that infusion of rat amylin was associated with greater renal vasodilation and less mesenteric vasoconstriction than is seen with infusion of human α-CGRP. They concluded that, by promoting renal hyperemia to a greater extent than did α-CGRP, rat amylin could cause less marked stimulation of the renin-angiotensin system, and thus, less secondary angiotensin II-mediated vasoconstriction. It was also noted, however, that during coinfusion of human α-$^{8-37}$CGRP (SEQ ID NO:16) and rat amylin, renal and mesenteric vasoconstrictions were unmasked, presumably due to unopposed vasoconstrictor effects of angiotensin II, and that this finding is similar to that seen during coinfusion of human α-CGRP and human α-$^{8-37}$CGRP (SEQ ID NO:16) (id. at 951).

Amylin has also been reported to have effects both on isolated osteoclasts where it caused cell quiescence, and in vivo where it was reported to lower plasma calcium by up to 20% in rats, in rabbits, and in humans with Paget's disease (see, e.g., Zaidi et al., *Trends in Endocrinal. and Metab.*, 4:255-259 (1993). From the available data, amylin seems to be 10 to 30 times less potent than human calcitonin for these actions. Interestingly, it was reported that amylin appeared to increase osteoclast cAMP production but not to increase cytosolic $Ca^{2+}$, while calcitonin does both (Alam et al., *Biochem. Biophys. Res. Commun.*, 179(1):134-139 (1991)). It was suggested, though not established, that calcitonin may act via two receptor types and that amylin may interact with one of these.

It has also been discovered that, surprisingly in view of its previously described renal vasodilator and other properties, amylin markedly increases plasma renin activity in intact rats when given subcutaneously in a manner that avoids any disturbance of blood pressure. This latter point is important because lowered blood pressure is a strong stimulus to renin release. Amylin antagonists, such as amylin receptor antagonists, including those selective for amylin receptors compared to CGRP and/or calcitonin receptors, can be used to block the amylin-evoked rise of plasma renin activity. The use of amylin antagonists to treat renin-related disorders is described in U.S. Pat. No. 5,376,638, issued Dec. 27, 1994.

In normal humans, fasting amylin levels from 1 to 10 pM and post-prandial or post-glucose levels of 5 to 20 pM have been reported (e.g., Hartter et al., *Diabetologia*, 34:52-54 (1991); Sanke et al., *Diabetologia*, 34:129-132 (1991); Koda et al., *The Lancet*, 339:1179-1180 (1992)). In obese, insulin-resistant individuals, post-food amylin levels can go higher, reaching up to about 50 pM. For comparison, the values for fasting and post-prandial insulin are 20 to 50 pM, and 100 to 300 pM respectively in healthy people, with perhaps 3- to 4-fold higher levels in insulin-resistant people. In Type 1 diabetes, where beta cells are destroyed, amylin levels are at or below the levels of detection and do not rise in response to glucose (Koda et al., *The Lancet*, 339:1179-1180 (1992)). In normal mice and rats, basal amylin levels have been reported from 30 to 100 pM, while values up to 600 pM have been measured in certain insulin-resistant, diabetic strains of rodents (e.g., Huang et al., *Hypertension*, 19:I-101-I-109 (1991); Gill et al., *Life Sciences*, 48:703-710 (1991)).

Injected into the brain, or administered peripherally, amylin has been reported to suppress food intake, e.g., Chance et al., *Brain Res.*, 539:352-354 (1991) and Chance et al., *Brain Res.*, 607:185-188 (1993), an action shared with CGRP and calcitonin. The effective concentrations at the cells that mediate this action are not known. Since the work described by the inventors herein with regard to the effect of amylin and amylin agonists to decrease body weight in humans, several publications have reported that infusion of amylin can cause anorexia in rats. See Arnelo et al., *Am. J. Physiol.*, 40:R1654-R1659 (1996); Arnelo et al., *Scan. J. Gastroenterol.*, 31:83-89 (1996).

Obesity

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, Acanthosis nigricans, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease. Rissanen et al., *British Medical Journal,* 301: 835-837 (1990).

Obesity, and especially upper body obesity, is a common and very serious public health problem in the United States and throughout the world. According to recent statistics, more than 25% of the United States population and 27% of the Canadian population are over weight. Kuczmarski, *Amer. J. of Clin. Nut.* 55:495 S-502S (1992); Reeder et. al., *Can. Med. Ass. J.,* 23:226-233 (1992). Upper body obesity is the strongest risk factor known for type II diabetes mellitus, and is a strong risk factor for cardiovascular disease and cancer as well. Recent estimates for the medical cost of obesity are $150,000,000,000 world wide. The problem has become serious enough that the surgeon general has begun an initiative to combat the ever increasing adiposity rampant in American society.

Much of this obesity induced pathology can be attributed to the strong association with dyslipidemia, hypertension, and insulin resistance. Many studies have demonstrated that reduction in obesity by diet and exercise reduces these risk factors dramatically. Unfortunately these treatments are largely unsuccessful with a failure rate reaching 95%. This failure may be due to the fact that the condition is strongly associated with genetically inherited factors that contribute to increased appetite, preference for highly caloric foods, reduced physical activity, and increased lipogenic metabolism. This indicates that people inheriting these genetic traits are prone to becoming obese regardless of their efforts to combat the condition. Therefore, a new pharmacological agent that can correct this adiposity handicap and allow the physician to successfully treat obese patients in spite of their genetic inheritance is needed.

Existing therapies for obesity include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery. Jung and Chong, *Clinical Endocrinology,* 35: 11-20 (1991); Bray, *Am. J. Clin. Nutr.,* 55: 538S-544S (1992). Protein-sparing modified fasting has been reported to be effective in weight reduction in adolescents. Lee et al., *Clin. Pediatr.,* 31: 234-236 (April 1992). Caloric restriction as a treatment for obesity causes catabolism of body protein stores and produces negative nitrogen balance. Protein-supplemented diets, therefore, have gained popularity as a means of lessening nitrogen loss during caloric restriction. Because such diets produce only modest nitrogen sparing, a more effective way to preserve lean body mass and protein stores is needed. In addition, treatment of obesity would be improved if such a regimen also resulted in accelerated loss of body fat. Various approaches to such treatment include those discussed by Weintraub and Bray, *Med. Clinics N. Amer.,* 73:237 (1989); Bray, *Nutrition Reviews,* 49:33 (1991).

Considering the high prevalence of obesity in our society and the serious consequences associated therewith as discussed above, any therapeutic drug potentially useful in reducing weight of obese persons could have a profound beneficial effect on their health. There is a need for a drug that will reduce total body weight of obese subjects toward their ideal body weight and help maintain the reduced weight level.

SUMMARY OF THE INVENTION

We have now discovered, surprisingly, that amylin, as well as amylin agonists, for example, the amylin agonist analogue $^{25,28,29}$Pro-h-amylin (SEQ ID NO:1) (also referred to as "pramlintide" and previously referred to as "AC-0137"), can be used for treatment of obesity in humans.

The present invention is directed to novel methods for treating or preventing obesity in humans comprising the administration of an amylin or an amylin agonist, for example, the amylin agonist analogue $^{25,28,29}$Pro-h-amylin. The amylin or amylin agonist may be administered alone or in conjunction with another obesity relief agent. In one aspect, the invention is directed to a method of treating obesity in a human subject comprising administering to said subject an effective amount of an amylin or such an amylin agonist. By "treating or preventing" is meant the management and care of a patient for the purpose of combating the disease, condition or disorder, and includes the administration of an amylin or an amylin agonist to prevent the onset of symptoms or complications, alleviating the symptoms or complications, or eliminating the disease condition or disorder. Treating or preventing obesity therefor includes the inhibition of weight gain and inducing weight loss in patients in need thereof. Additionally, treating or preventing obesity is meant to include controlling weight for cosmetic purposes in humans, that is to control body weight to improve bodily appearance.

The term "amylin" is understood to include compounds such as those defined in U.S. Pat. No. 5,234,906, issued Aug. 10, 1993, for "Hyperglycemic Compositions," the contents of which are hereby incorporated by reference. For example, it includes the human peptide hormone referred to as amylin and secreted from the beta cells of the pancreas, and species variations of it.

"Amylin agonist" is also a term known in the art, and refers to a compound which mimics effects of amylin. An amylin agonist may be a peptide or a non-peptide compound, and includes amylin agonist analogues.

The term "amylin agonist analogue" is understood to refer to derivatives of an amylin which act as amylin agonists, normally, it is presently believed, by virtue of binding to or otherwise directly or indirectly interacting with an amylin receptor or other receptor or receptors with which amylin itself may interact to elicit a biological response. Useful amylin agonist analogues include those identified in an International Application, WPI Acc. No. 93-182488/22, entitled "New Amylin Agonist Peptides Used for Treatment and Prevention of Hypoglycemia and Diabetes Mellitus," the contents of which is also hereby incorporated by reference.

Further, amylin agonist analogues useful in the methods of this application include amylin agonist analogues having the following amino acid sequence (SEQ ID NO:23):

$^1$A$_1$-X-Asn-Thr-$^5$Ala-Thr-Y-Ala-Thr-$^{10}$Gln-Arg-Leu-

B$_1$-Asn-$^{15}$Phe-Leu-C$_1$-D$_1$-E$_1$-$^{20}$F$_1$-G$_1$-Asn-H$_1$-Gly-$^{25}$I$_1$-J$_1$-

Leu-K$_1$-L$_1$-$^{30}$Thr-M$_1$-Val-Gly-Ser-$^{35}$Asn-Thr-Tyr-Z wherein:
A$_1$ is hydrogen Lys, Ser, Ala, des-α-amino Lys, or acetylated Lys;
B$_1$ is Ala, Ser or Thr;
C$_1$ is Val, Leu or Ile;

$D_1$ is His or Arg;
$E_1$ is Ser or Thr;
$F_1$ is Ser, Thr, Gln or Asn;
$G_1$ is Asn, Gln or His;
$H_1$ is Phe, Leu or Tyr;
$I_1$ is Ala or Pro;
$J_1$ is Ile, Val, Ala or Leu;
$K_1$ is Ser, Pro, Leu, Ile or Thr;
$L_1$ is Ser, Pro or Thr;
$M_1$ is Asn, Asp or Gln;
X and Y are independently selected residues having side chains which are chemically bonded to each other to form an intramolecular linkage; and
Z is hydroxy, amino, alkylamino, dialkylamino, cycloalkylamino, arylamino, aralkylamino, alkyloxy, aryloxy or aralkyloxy;
provided that:
(a) when $A_1$ is Lys, $B_1$ is Ala, $C_1$ is Val, $D_1$ is His, $E_1$ is Ser, $F_1$ is Ser, $G_1$ is Asn, $H_1$ is Phe, $I_1$ is Ala, $J_1$ is Ile, $K_1$ is Ser, $L_1$ is Ser, and $M_1$ is Asn;
(b) when $A_1$ is Lys, $B_1$ is Ala, $C_1$ is Ile, $D_1$ is Arg, $E_1$ is Ser, $F_1$ is Ser, $G_1$ is Asn, $H_1$ is Leu, $I_1$ is Ala, $J_1$ is Ile, $K_1$ is Ser, $L_1$ is Pro, and $M_1$ is Asn;
(c) when $A_1$ is Lys, $B_1$ is Ala, $C_1$ is Val, $D_1$ is Arg, $E_1$ is Thr, $F_1$ is Ser, $G_1$ is Asn, $H_1$ is Leu, $I_1$ is Ala, $J_1$ is Ile, $K_1$ is Ser, $L_1$ is Pro, and $M_1$ is Asn;
(d) when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val, $K_1$ is Pro, $L_1$ is Pro, and $M_1$ is Asn;
(e) when $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Pro, $J_1$ is Val, $K_1$ is Ser, $L_1$ is Pro and $M_1$ is Asn; or
(f) when $A_1$ is Lys, $B_1$ is Thr, $C_1$ is Val, $D_1$ is Arg, $E_1$ is Ser, $F_1$ is Ser, $G_1$ is His, $H_1$ is Leu, $I_1$ is Ala, $J_1$ is Ala, $K_1$ is Leu, $L_1$ is Pro and $M_1$ is Asp;
then one or more of any of $A_1$ to $M_1$ is not an L-amino acid and Z is not amino.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

As used herein, the following terms have the following meanings unless expressly stated to the contrary:

The term "alkyl" refers to both straight- and branched-chain alkyl groups. The term "lower alkyl" refers to both straight- and branched-chain alkyl groups having a total of from 1 to 6 carbon atoms and includes primary, secondary, and tertiary alkyl groups. Typical lower alkyls include, for example, methyl, ethyl, n-propyl, isopropyl, n-butyl, isobutyl, t-butyl, n-pentyl, n-hexyl, and the like.

The term "aryl" refers to carbocyclic aromatic groups of 6 to 14 carbon atoms such as phenyl and naphthyl, as well as heterocyclic aromatic groups containing 1 to 3 heteroatoms (nitrogen, oxygen, sulfur, etc.) such as pyridyl, triazolopyrazine, pyrimidine and the like.

The term "aralkyl" refers to an "aryl" group of 6 to 10 carbon atoms directly attached to an "alkyl" group of 1 to 4 carbon atoms and includes for example benzyl, p-chlorobenzyl, p-methylbenzyl, and 2-phenylethyl.

The term "cycloalkyl" refers to cyclic alkyl groups of 5 to 8 carbon atoms.

Biologically active derivatives of the above agonist analogues are also included within the scope of amylin agonist analogues useful in the present invention in which the stereochemistry of individual amino acids may be inverted from (L)/S to (D)/R at one or more specific sites. Also included within the scope of amylin agonist analogues useful in the present invention are the agonist analogues modified by glycosylation of Asn, Ser and/or Thr residues.

Biologically active agonist analogues of amylin which contain less peptide character are also included in the scope of amylin agonist analogues useful in the present invention. Such peptide mimetics may include, for example, one or more of the following substitutions for —CO—NH— amide bonds: depsipeptides (—CO—O—), iminomethylenes (—CH$_2$—NH—), trans-alkenes (—CH═CH—), β-enaminonitriles (—C(═CH—CN)—NH—), thioamides (—CS—NH—), thiomethylenes (—S—CH$_2$— or —CH$_2$—S—), methylenes, and retro-amides (—NH—CO—).

The above-described amylin agonist analogues form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid, and camphorsulfonic acid. Salts prepared with bases include, for example, ammonium salts, alkali metal salts (such as sodium and potassium salts), and alkali earth salts (such as calcium and magnesium salts). Acetate, hydrochloride, and trifluoroacetate salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin. The above-described amylin agonist analogues include various stereoisomers. In the preferred amylin agonist analogues, the chiral centers on the peptide backbone are all S.

In a preferred embodiment, the amylin agonist is an amylin agonist analogue, preferably, [25, 28, 29]Pro-h-amylin (SEQ ID NO:1).

DETAILED DESCRIPTION OF THE INVENTION

The study described in Example 1 showed that administration of the amylin agonist [25,28,29]Pro-h-amylin (pramlintide) to insulin-using Type 2 diabetics resulted in a decrease in body weight which achieved statistical significance within two dosage groups, 60 μg TID and 60 μg QID. This is in sharp contrast to treatment with insulin alone in patients with Type II diabetes, which is usually associated with weight gain.

Amylin agonist analogues useful in this invention include amylin agonist analogues disclosed in the above-noted WPI Acc. No. 93-182488/22, "New Amylin Agonist Peptides Used for Treatment and Prevention of Hypoglycemia and Diabetes Mellitus." Amylin agonists include agonist analogues of amylin as follows:

1. An agonist analogue of amylin having the amino acid sequence (SEQ ID NO:17):

[1]$A_1$-X-Asn-Thr-[5]Ala-Thr-Y-Ala-Thr-[10]Gln-Arg-Leu- $B_1$-Asn-[15]Phe-Leu-$C_1$-$D_1$-$E_1$-[20]$F_1$-$G_1$-Asn-$H_1$-Gly-[25]Pro- $I_1$-Leu-Pro-$J_1$-[30]Thr-$K_1$-Val-Gly-Ser-[35]Asn-Thr-Tyr-Z wherein
$A_1$ is Lys, Ala, Ser or hydrogen;
$B_1$ is Ala, Ser or Thr;
$C_1$ is Val, Leu or Ile;
$D_1$ is His or Arg;

$E_1$ is Ser or Thr;
$F_1$ is Ser, Thr, Gln or Asn;
$G_1$ is Asn, Gln or His;
$H_1$ is Phe, Leu or Tyr;
$I_1$ is Ile, Val, Ala or Leu;
$J_1$ is Ser, Pro or Thr;
$K_1$ is Asn, Asp or Gln;
X and Y are independently selected residues having side chains which are chemically bonded to each other to form an intramolecular linkage, wherein said intramolecular linkage comprises a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val, $J_1$ is Pro, and $K_1$ is Asn; then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

2. An agonist analogue of amylin having the amino acid sequence (SEQ ID NO:18):

$^1A_1$-X-Asn-Thr-$^5$Ala-Thr-Y-Ala-Thr-$^{10}$Gln-Arg-Leu- $B_1$-Asn-$^{15}$Phe-Leu-$C_1$-$D_1$-$E_1$-$^{20}F_1$-$G_1$-Asn-$H_1$-Gly-$^{25}$Pro- $I_1$-Leu-$J_1$-Pro-$^{30}$Thr-$K_1$-Val-Gly-Ser-$^{35}$Asn-Thr-Tyr-Z wherein
$A_1$ is Lys, Ala, Ser or hydrogen;
$B_1$ is Ala, Ser or Thr;
$C_1$ is Val, Leu or Ile;
$D_1$ is His or Arg;
$E_1$ is Ser or Thr;
$F_1$ is Ser, Thr, Gln or Asn;
$G_1$ is Asn, Gln or His;
$H_1$ is Phe, Leu or Tyr;
$I_1$ is Ile, Val, Ala or Leu;
$J_1$ is Ser, Pro, Leu, Ile or Thr;
$K_1$ is Asn, Asp or Gln;
X and Y are independently selected residues having side chains which are chemically bonded to each other to form an intramolecular linkage, wherein said intramolecular linkage comprises a disulfide bond, a lactam or a thioether linkage; and Z is amino, alkylamino, dialkylamino, cycloalkylamino, arylamino, aralkylamino, alkyloxy, aryloxy or aralkyloxy; and provided than when
(a) $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val, $J_1$ is Pro and $K_1$ is Asn; or
(b) $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Val, $J_1$ is Ser and $K_1$ is Asn;
then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

3. An agonist analogue of amylin having the amino acid sequence (SEQ ID NO:19):

$^1A_1$-X-Asn-Thr-$^5$Ala-Thr-Y-Ala-Thr-$^{10}$Gln-Arg-Leu- $B_1$-Asn-$^{15}$Phe-Leu-$C_1$-$D_1$-$E_1$-$^{20}F_1$-$G_1$-Asn-$H_1$-Gly-$^{25}I_1$-

$J_1$-Leu-Pro-Pro-$^{30}$Thr-$K_1$1-Val-Gly-Ser-$^{35}$Asn-Thr-

Tyr-Z wherein
$A_1$ is Lys, Ala, Ser or hydrogen;
$B_1$ is Ala, Ser or Thr;
$C_1$ is Val, Leu or Ile;
$D_1$ is His or Arg;
$E_1$ is Ser or Thr;
$F_1$ is Ser, Thr, Gln or Asn;
$G_1$ is Asn, Gln or His;
$H_1$ is Phe, Leu or Tyr;
$I_1$ is Ala or Pro;
$J_1$ is Ile, Val, Ala or Leu;
$K_1$ is Asn, Asp or Gln;
X and Y are independently selected residues having side chains which are chemically bonded to each other to form an intramolecular linkage, wherein said intramolecular linkage comprises a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val and $K_1$ is Asn; then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

4. An agonist analogue of amylin having the amino acid sequence (SEQ ID NO:20):

$^1A_1$-X-Asn-Thr-$^5$Ala-Thr-Y-Ala-Thr-$^{10}$Gln-Arg-Leu- $B_1$-Asn-$^{15}$Phe-Leu-$C_1$-$D_1$-$E_1$-$^{20}F_1$-$G_1$-Asn-$H_1$-Gly-$^{25}$Pro- $I_1$-Leu-Pro-Pro-$^{30}$Thr-$J_1$-Val-Gly-Ser-$^{35}$Asn-Thr-Tyr-Z wherein
$A_1$ is Lys, Ala, Ser or hydrogen;
$B_1$ is Ala, Ser or Thr;
$C_1$ is Val, Leu or Ile;
$D_1$ is His or Arg;
$E_1$ is Ser or Thr;
$F_1$ is Ser, Thr, Gln or Asn;
$G_1$ is Asn, Gln or His;
$H_1$ is Phe, Leu or Tyr;
$I_1$ is Ile, Val, Ala or Leu;
$J_1$ is Asn, Asp or Gln;
X and Y are independently selected residues having side chains which are chemically bonded to each other to form an intramolecular linkage wherein said intramolecular linkage comprises a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val and $J_1$ is Asn; then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

Preferred amylin agonist analogues include $^{25,28,29}$Pro-h-amylin (SEQ ID NO:1), $^{18}$Arg$^{25,28,29}$Pro-h-amylin (SEQ ID NO:2) and $^{18}$Arg$^{25,28}$Pro-h-amylin (SEQ ID NO:3).

Activity as amylin agonists can be confirmed and quantified by performing various screening assays, including the nucleus accumbens receptor binding assay described below in Example 5, followed by the soleus muscle assay described below in Example 6, a gastric emptying assay described below in Example 7 or 8, or by the ability to induce hypocalcemia or reduce postprandial hyperglycemia in mammals, as described herein.

The receptor binding assay, a competition assay which measures the ability of compounds to bind specifically to membrane-bound amylin receptors, is described in U.S. Pat. No. 5,264,372, issued Nov. 23, 1993, the disclosure of which is incorporated herein by reference. The receptor binding assay is also described in Example 2 below. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (INPLOT program; GRAPHPAD Software, San Diego, Calif.) or the ALLFIT program of DeLean et al. (ALLFIT, Version 2.7 (NIH, Bethesda, Md. 20892)). Munson and Rodbard, *Anal. Biochem.* 107:220-239 (1980).

Assays of biological activity of amylin agonists in the soleus muscle may be performed using previously described methods (Leighton, B. and Cooper, *Nature,* 335:632-635 (1988); Cooper, et al., *Proc. Natl. Acad. Sci. USA* 85:7763-7766 (1988)), in which amylin agonist activity may be assessed by measuring the inhibition of insulin-stimulated glycogen synthesis. The soleus muscle assay is also described in Example 6 below.

Methods of measuring the rate of gastric emptying are disclosed in, for example, Young et al., *Diabetologia*, 38(6): 642-648 (1995). In a phenol red method, which is described in Example 7 below, conscious rats receive by gavage an acoloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, which is described in Example 8 below, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Effects of amylins or amylin agonists on body weight can be identified, evaluated, or screened for using the methods described in Example 1 below, or other art-known or equivalent methods for determining effect on body weight. Preferred amylin agonist compounds exhibit activity in the receptor binding assay on the order of less than about 1 to 5 nM, preferably less than about 1 nM and more preferably less than about 50 pM. In the soleus muscle assay, preferred amylin agonist compounds show $EC_{50}$ values on the order of less than about 1 to 10 micromolar. In the gastric emptying assays, preferred agonist compounds show $ED_{50}$ values on the order of less than 100 μg/rat.

Amylin and peptide amylin agonists may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-2N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys (Cl-Z), Fmoc-Lys(Boc), Boc-Glu(Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, methylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and Tboc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−5 EC to 0 EC, 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6-12). Peptides may be also be assembled using an Advanced Chem Tech Synthesizer (Model MPS 350, Louisville, Ky.).

Peptides may be purified by RP-HPLC (preparative and analytical) using a Waters DELTA PREP 3000 system. A C4, C8 or C18 preparative column (10 F, 2.2×25 cm; Vydac, Hesperia, Calif.) may be used to isolate peptides, and purity may be determined using a C4, C8 or C18 analytical column (5 F, 0.46×25 cm; Vydac). Solvents (A=0.1% TFA/water and B=0.1% TFA/$CH_3CN$) may be delivered to the analytical column at a flowrate of 1.0 ml/min and to the preparative column at 15 ml/min. Amino acid analyses may be performed on the Waters PICO TAG system and processed using the MAXIMA program. Peptides may be hydrolyzed by vapor-phase acid hydrolysis (115 EC, 20-24 h). Hydrolysates may be derivatized and analyzed by standard methods (Cohen, et al., *The Pico Tag Method: A Manual of Advanced Techniques for Amino Acid Analysis*, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems BIO-ION 20 mass spectrometer.

Peptide compounds useful in the invention may also be prepared using recombinant DNA techniques, using methods now known in the art. See, e.g., Sambrook et al., *Molecular Cloning: A Laboratory Manual,* 2d Ed., Cold Spring Harbor (1989). Non-peptide compounds useful in the present invention may be prepared by art-known methods.

The compounds referenced above may form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Compositions useful in the invention may conveniently be provided in the form of formulations suitable for parenteral (including intravenous, intramuscular and subcutaneous) or nasal or oral administration. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988). Compounds provided as parenteral compositions for injection or infusion can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

Preferably, these parenteral dosage forms are prepared according to the commonly owned patent application entitled, "Parenteral, Liquid Formulations for Amylin Agonist Peptides," Ser. No. 60/035,140, filed Jan. 8, 1997, which is incorporated herein by this reference, and include approximately 0.01 to 0.2 w/v %, respectively, of an amylin or an amylin agonist in a aqueous system along with approximately 0.02 to 0.5 w/v % of an acetate, phosphate, citrate or glutamate buffer to obtain a pH of the final composition of approximately 3.0 to 6.0 (more preferably 3.0 to 5.5), as well as approximately 1.0 to 10 w/v % of a carbohydrate or polyhydric alcohol stabilizer in an aqueous continuous phase. Approximately 0.005 to 1.0 w/v % of an antimicrobial preservative selected from the group consisting of m-cresol, benzyl alcohol, methyl, ethyl, propyl and butyl parabens and phenol is also present in the preferred formulation of product designed to allow the patient to withdraw multiple doses. A sufficient amount of water for injection is used to obtain the desired concentration of solution. Sodium chloride, as well as other excipients, may also be present, if desired. Such excipients, however, must maintain the overall stability of the amylin or amylin agonist peptide. Most preferably, in the amylin or amylin agonist formulation for parenteral administration, the polyhydric alcohol is mannitol, the buffer is an acetate buffer, the preservative is approximately 0.1 to 0.3 w/v % of m-cresol, and the pH is approximately 3.7 to 4.3.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a TWEEN), or an ionic surfactant (such as alkali polyether alcohol sulfates or sulfonates, a TRITON).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an amylin or amylin agonist, for example, an amylin agonist analogue compound which will be effective in one or multiple doses to control obesity at the selected level. Therapeutically effective amounts of an amylin or amylin agonist, such as an amylin agonist analogue, for use in the control of obesity are those that decrease body weight. As will be recognized by those in the field, an effective amount of therapeutic agent will vary with many factors including the age and weight of the patient, the patient's physical condition, the action to be obtained and other factors.

The effective single, divided or continuous analgesic doses of the compounds, for example, including $^{25,28,29}$Pro-h-amylin, $^{18}$Arg$^{25,28,29}$Pro-h-amylin and $^{18}$Arg$^{25,28}$Pro-h-amylin will typically be in the range of 0.01 or 0.03 to about 5 mg/day, preferably about 0.01 or 0.5 to 2 mg/day and more preferably about 0.01 or 0.1 to 1 mg/day, for a 70 kg patient, administered in a single, divided or continuous doses. The exact dose to be administered is determined by the attending clinician and is dependent upon a number of factors, including, these noted above. Administration should begin at the first sign of obesity. Administration may be by injection or infusion, preferably intravenous, subcutaneous or intramuscular. Orally active compounds may be taken orally, however dosages should be increased 5-10 fold.

Generally, in treating or preventing obesity, the compounds of this invention may be administered to patients in need of such treatment in a dosage ranges similar to those given above, however, the compounds may be administered more frequently, for example, one, two, or three times a day or continuously. Preferably, the doses of peptide agonists, for example, pramlintide, are administered subcutaneously in 30-300 μg doses given from one to four times a day, and more preferably from 30-120 μg doses given two to four times per day.

To assist in understanding the present invention, the following Example is included which describes the results of a set of experiments. The studies relating to this invention should not, of course, be construed as specifically limiting the invention and such variations of the invention, now known or later developed, which would be within the purview of one skilled in the art are considered to fall within the scope of the invention as described herein and hereinafter claimed.

Example 1

Measurement of Body Weight

Study participants were males and females 25 to 78 years of age with a history of Type II diabetes mellitus requiring treatment with insulin for at least 6 months prior to the pre-screening visit. Patients had a body weight not varying more than 45% from the desirable weight before admission into the study (based upon Metropolitan Life Tables). The study employed methods described in Thompson et al., *Diabetes* 46:632-636 (1997). Following a placebo lead-in period, patients were randomized to receive placebo or one of three dose regimens of $^{25,28,29}$Pro-h-amylin (pramlintide) for 4 weeks: 30 μg QID (before breakfast, lunch, dinner and evening snack), 60 μg TID (before breakfast, lunch and dinner) or 60 μg QID (before breakfast, lunch, dinner and evening snack). Throughout the study drug period, patients self-administered four injections of study drug daily, within 15 minutes of each meal and the evening snack. During the double-blind period, patients randomized to pramlintide 60 µg TID administered placebo before the evening snack. Both pramlintide and placebo were administered as separate injections into the subcutaneous tissue of the anterior abdominal wall; the specific site was alternated after each injection. Patients were instructed to remain on their usual diet, insulin and exercise regimens throughout the study, unless otherwise instructed by the investigator, and to abstain from alcoholic beverages prior to all clinic visits.

As shown in Table I, there was a statistically significant weight reduction from baseline to Week 4 within the pramlintide 60 µg TID (mean=−0.89 kg, p=0.0056) and pramlintide 60 µg QID (mean=−0.72 kg, p=0.0014) groups. With the Hochberg adjustment for multiple comparisons, there was no statistically significant change in body weight from baseline to Week 4 in any of the three pramlintide groups compared to the placebo group. Thus, pramlintide administration with continued insulin use improved glycemic control with a decrease in body weight which achieved statistical significance within the 60 µg TID and QID groups. This is in sharp contrast to improved glucose control achieved with insulin alone in patients with Type II diabetes which is usually associated with weight gain.

TABLE I

Body Weight: Change from Baseline to Week 4

| Treatment Group | N | Baseline Mean (kg) | Change at Week 4 Mean (kg) | Change at Week 4 Median (kg) | p-Value* Within Study Drug Group | p-Value* Placebo Comparison |
| --- | --- | --- | --- | --- | --- | --- |
| Placebo | 47 | 87.0 | −0.04 | 0.0 | NS | NAP |
| Pramlintide 30 µg QID | 47 | 88.5 | −0.36 | −0.45 | NS | NS |
| Pramlintide 60 µg TID | 48 | 86.2 | −0.89 | −1.05 | 0.0056 | NS |
| Pramlintide 60 µg QID | 51 | 91.5 | −0.72 | −0.45 | 0.0014 | NS |

*Student's t-test (within study-drug group comparison). Two-way ANOVA (placebo comparison) with the Hochberg Adjustment.
NS = Not statistically significant;
NAP = Not applicable.

Example 2

Preparation of $^{25,28,29}$Pro-h-Amylin (SEQ ID NO:1)

Solid phase synthesis of $^{25,28,29}$Pro-h-amylin (SEQ ID NO:1) using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{25,28,29}$Pro-h-amylin (SEQ ID NO:1) was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3{,}949$.

Example 3

Preparation of $^{18}$Arg$^{25,28,29}$Pro-h-Amylin (SEQ ID NO:2)

Solid phase synthesis of $^{18}$Arg$^{25,28,29}$Pro-h-amylin (SEQ ID NO:2) using methylbenzhydrylamine anchor-bond resin and $N^\alpha$-Boc/benzyl-side chain protection was carried out by standard peptide synthesis methods. The $^{2,7}$-[disulfide]-amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28,29}$Pro-h-amylin (SEQ ID NO:2) was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3{,}971$.

Example 4

Preparation of $^{18}$Arg$^{25,28}$Pro-h-Amylin (SEQ ID NO:3)

Solid phase synthesis of $^{18}$Arg$^{25,28}$Pro-h-amylin (SEQ ID NO:3) using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28}$Pro-h-amylin (SEQ ID NO:3) was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3{,}959$.

Example 5

Receptor Binding Assay

Evaluation of the binding of compounds to amylin receptors was carried out as follows. $^{125}$I-rat amylin (SEQ ID NO:21) (Bolton-Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200-250 grams) were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$I-amylin (SEQ ID NO:22) binding, membranes from 4 mg original wet weight of tissue were incubated with $^{125}$I-amylin (SEQ ID NO:22) at 12-16 pM in 20 mM HEPES buffer containing 0.5 mg/ml bacitracin, 0.5 mg/ml bovine serum albumin, and 0.2 mM PMSF. Solutions were incubated for 60 minutes at 23° C. Incubations were terminated by filtration through GF/B glass fiber filters (Whatman Inc., Clifton, N.J.) which had been presoaked for 4 hours in 0.3% polyethyleneimine in order to reduce non-specific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$ M unlabeled test compound and were analyzed by nonlinear regression using a 4-parameter logistic equation (INPLOT program; GRAPHPAD Software, San Diego).

In this assay, purified human amylin binds to its receptor at a measured $IC_{50}$ of about 50 pM. Results for test compounds are set forth in Table II, showing that each of the compounds has significant receptor binding activity.

Example 6

Soleus Muscle Assay

Determination of amylin agonist activity of compounds was carried out using the soleus muscle assay as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The tendo achilles was cut just above os calcis and m. gastrocnemius reflected out from the posterior aspect of the tibia. M soleus, a small 15-20 mm long, 0.5 mm thick flat muscle on the bone surface of m. gastrocnemius was then stripped clear and the perimysium cleaned off using fine scissors and forceps. M soleus was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstrable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 5.94 mmol (443 mg), $CaCl_2$ 2.54 mmol (282 mg), $MgSO_4$ 1.19 mmol (143 mg), $KH_2PO_4$ 1.19 mmol (162 mg), $NaHCO_3$ 25 mmol (2.1 g), 5.5 mmol glucose (1 g) and recombinant human insulin (HUMULIN-R, Eli Lilly, Ind.) and the test compound, as detailed below. pH at 37 EC was verified as being between 7.1 and 7.4. Muscles were assigned to different flasks so that the 4 muscle pieces from each animal were evenly distributed among the different assay conditions. The incubation media were gassed by gently blowing carbogen (95% $O_2$, 5% $CO_2$) over the surface while being continuously agitated at 37° C. in an oscillating water bath. After a half-hour "preincubation" period, 0.5 μCi of U-$^{14}$C-glucose was added to each flask which was incubated for a further 60 minutes. Each muscle piece was then rapidly removed, blotted and frozen in liquid $N_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70° C. for 45 minutes under continuous agitation. Dissolved glycogen was precipitated out onto the vial by the addition of 3 mL absolute ethanol and overnight cooling at −20° C. The supernatant was gently aspirated, the glycogen washed again with ethanol, aspirated and the precipitate dried under vacuum. All ethanol is evaporated to avoid quenching during scintillation counting. The remaining glycogen was redissolved in 1 mL water and 4 mL scintillation fluid and counted for $^{14}$C.

The rate of glucose incorporation into glycogen (expressed in μmol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (ALLFIT, v2.7, NIH, MD) to derive $EC_{50}$'s. Since $EC_{50}$ is log-normally distributed, it is expressed ±standard error of the logarithm. Pairwise comparisons were performed using t-test based routines of SYSTAT (Wilkinson, "SYSTAT: the system for statistics," SYSTAT Inc., Evanston Ill. (1989)).

Dose response curves were generated with muscles added to media containing 7.1 nM (1000 μU/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at −70° C.

Human amylin is a known hyperglycemic peptide, and $EC_{50}$ measurements of amylin preparations in the soleus muscle assay range typically from about 1-10 nM, although some commercial preparations which are less than 90% pure have higher $EC_{50}$'s due to the presence of contaminants that result in a lower measured activity. Results for test compounds are set forth in Table II.

TABLE II

| | | Receptor Binding Assay $IC_{50}$ (pM) | Soleus Muscle Assay $EC_{50}$ (nM) |
|---|---|---|---|
| 1) | $^{28}$Pro-h-Amylin (SEQ ID NO: 4) | 15.0 | 2.64 |
| 2) | $^{25}$Pro$^{26}$Val$^{28,29}$Pro-h-Amylin (SEQ ID NO: 5) | 18.0 | 4.68 |
| 3) | $^{2,7}$Cyclo-[$^2$Asp, $^7$Lys]-h-Amylin (SEQ ID NO: 6) | 310.0 | 6.62 |
| 4) | $^{2-37}$h-Amylin (SEQ ID NO: 7) | 236.0 | 1.63 |
| 5) | $^1$Ala-h-Amylin (SEQ ID NO: 8) | 148.0 | 12.78 |
| 6) | $^1$Ser-h-Amylin (SEQ ID NO: 9) | 33.0 | 8.70 |
| 7) | $^{29}$Pro-h-Amylin (SEQ ID NO: 10) | 64.0 | 3.75 |
| 8) | $^{25,28}$Pro-h-Amylin (SEQ ID NO: 11) | 26.0 | 13.20 |
| 9) | des-$^1$Lys$^{25,28}$Pro-h-Amylin (SEQ ID NO: 12) | 85.0 | 7.70 |
| 10) | $^{18}$Arg$^{25,28}$Pro-h-Amylin (SEQ ID NO: 3) | 32.0 | 2.83 |
| 11) | des-$^1$Lys$^{18}$Arg$^{25,28}$Pro-h-Amylin (SEQ ID NO: 13) | 82.0 | 3.77 |
| 12) | $^{18}$Arg$^{25,28,29}$Pro-h-Amylin (SEQ ID NO: 2) | 21.0 | 1.25 |
| 13) | des-$^1$Lys$^{18}$Arg$^{25,28,29}$Pro-h-Amylin (SEQ ID NO: 14) | 21.0 | 1.86 |
| 14) | $^{25,28,29}$Pro-h-Amylin (SEQ ID NO: 1) | 10.0 | 3.71 |
| 15) | des-$^1$Lys$^{25,28,29}$Pro-h-Amylin (SEQ ID NO: 15) | 14.0 | 4.15 |

Example 7

Phenol Red Gastric Emptying Assay

Gastric emptying was measured using a modification (Plourde et al., *Life Sci.* 53:857-862 (1993)) of the original method of Scarpignato et al. (Arch. Int. Pharmacodyn. Ther. 246:286-295 (1980)). Briefly, conscious rats received by gavage. 1.5 mL of an acoloric gel containing 1.5% methyl cellulose (M-0262, Sigma Chemical Co., St. Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In most experiments, the stomach was clear. In other experiments, particulate gastric contents were centrifuged to clear the solution for absorbance measurements. Where the diluted gastric contents remained turbid, the spectroscopic absorbance due to phenol red was derived as the difference between that present in alkaline vs acetified diluent. In separate experiments on 7 rats, the stomach and small intestine were both excised and opened into an alkaline solution. The quantity of phenol red that could be recovered from the upper gastrointestinal tract within 29 minutes of gavage was 89±4%; dye which appeared to bind irrecoverably to the gut luminal surface may have accounted for the balance. To compensate for this small loss, percent of stomach contents remaining after 20 minutes were expressed as a fraction of the gastric contents recovered from control rats sacrificed immediately after gavage in the same experiment. Percent gastric emptying contents remaining=(absorbance at 20 min)/(absorbance at 0 min). Dose response curves for gastric emptying were fitted to a 4-parameter logistic model using a least-squares iterative routine (ALLFIT, v2.7, NIH, Bethesda, Md.) to derive $ED_{50}$s. Since $ED_{50}$ is log-normally distributed, it is expressed ±standard error of the logarithm. Pairwise comparisons were performed using one-way analysis of variance and the STUDENT-NEWMAN-KEULS multiple comparisons test (INSTAT v2.0, GRAPHPAD Software, San Diego, Calif.) using P<0.05 as the level of significance.

In dose response studies, rat amylin (Bachem, Torrance, Calif.) dissolved in 0.15 M saline, was administered as a 0.1 mL subcutaneous bolus in doses of 0, 0.01, 0.1, 1, 10 or 100 μg 5 minutes before gavage in Harlan Sprague Dawley (non-diabetic) rats fasted 20 hours and diabetic BB rats fasted 6 hours. When subcutaneous amylin injections were given 5 minutes before gavage with phenol red indicator, there was a dose-dependent suppression of gastric emptying (data not shown). Suppression of gastric emptying was complete in normal HSD rats administered 1 μg of amylin, and in diabetic rats administered 10 μg (P=0.22, 0.14). The $ED_{50}$ for inhibition of gastric emptying in normal rats was 0.43 μg (0.60 nmol/kg)±0.19 log units, and was 2.2 μg (2.3 nmol/kg)±0.18 log units in diabetic rats.

Example 8

Tritiated Glucose Gastric Emptying Assay

Conscious, non-fasted, Harlan Sprague Dawley rats were restrained by the tail, the tip of which was anesthetized using 2% lidocaine. Tritium in plasma separated from tail blood collected 0, 15, 30, 60, 90 and 120 minutes after gavage was detected in a beta counter. Rats were injected subcutaneously with 0.1 mL saline containing 0, 0.1, 0.3, 1, 10 or 100 μg of rat amylin 1 minute before gavage (n=8, 7, 5, 5, 5, respectively). After gavage of saline pre-injected rats with tritiated glucose, plasma tritium increased rapidly (t ½ of about 8 minutes) to an asymptote that slowly declined. Subcutaneous injection with amylin dose-dependently slowed and/or delayed the absorption of the label. Plasma tritium activity was integrated over 30 minutes to obtain the areas under the curve plotted as a function of amylin dose. The $ED_{50}$ derived from the logistic fit was 0.35 μg of amylin.

Preparation of des-$^1$Lys$^{25,28,29}$Pro-h-Amylin (SEQ ID NO:15)

Solid phase synthesis of des-$^1$Lys$^{25,28,29}$Pro-h-amylin (SEQ ID NO:15) using methylbenzhydrylamine anchor-bond resin and N$^\alpha$-Boc/benzyl-side chain protection was carried out by standard peptide synthesis methods. The $^{2,7}$-[disulfide] amylin-MBHA-resin was obtained by treatment of Acm-protected cysteines with thallium (III) trifluoroacetate in trifluoroacetic acid. After cyclization was achieved, the resin and side chain protecting groups were cleaved with liquid HF in the presence of dimethylsulfide and anisole. The des-$^1$Lys$^{25,}$ $_{28,29}$Pro-h-amylin (SEQ ID NO:15) was purified by preparative reversed-phase HPLC. The peptide was found to be homogeneous by analytical HPLC and capillary electrophoresis and the structure was confirmed by amino acid analysis and sequence analysis. The product gave the desired mass ion. FAB mass spec: $(M+H)^+$=3,823.

We claim:

1. A method of treating obesity in an obese human subject in need of said treatment consisting essentially of administering to said obese subject a therapeutically effective amount of pramlintide to decrease body weight after 4 four weeks of said treatment in said obese human subject from the body weight of said obese patient prior to said treatment, wherein said pramlintide in present in a composition comprising a pharmaceutically acceptable carrier, wherein from 0.5 to 2.0 mg/day of said pramlintide in said composition is administered to said obese subject from 1 to 4 times a day.

2. The method of claim 1, wherein said composition is administered two times per day.

3. The method of claim 1, wherein said composition is administered three times per day.

4. A method of treating obesity in an obese human subject in need of said treatment comprising administering to said obese subject a composition comprising a pharmaceutically acceptable carrier and a therapeutically effective amount of an obesity-relief agent consisting of pramlintide to decrease body weight after 4 four weeks of said treatment in said obese human subject from the body weight of said obese patient prior to said treatment, wherein from 0.5 to 2.0 mg/day of said pramlintide in said composition is administered to said obese subject from 1 to 4 times a day.

5. The method of claim 4, wherein said composition is administered three times per day.

6. A method of treating obesity in an obese human subject in need of said treatment comprising administering to said obese subject a therapeutically effective amount of pramlintide to decrease body weight after 4 four weeks of said treatment in said obese human subject from the body weight of said obese patient prior to said treatment, wherein said pramlintide is not administered in conjunction with another obesity-relief agent, wherein from 0.5 to 2.0 mg/day of said pramlintide is administered to said obese subject from 1 to 4 times a day.

7. A method of treating obesity in an obese human subject in need of said treatment comprising administering to said obese subject a therapeutically effective amount of a composition consisting essentially of pramlintide to decrease body weight after 4 four weeks of said treatment in said obese human subject from the body weight of said obese patient prior to said treatment, wherein from 0.5 to 2.0 mg/day of said pramlintide is administered to said obese subject from 1 to 4 times a day.

8. The method of claim 1, 4, 6 or 7, wherein said pramlintide is pramlintide trifluoroacetate, pramlintide acetate, or pramlintide-HCl.

9. The method of claim 4, 6 or 7, wherein said composition is administered two times per day.

10. The method of claim 4, 6, or 7, wherein said composition is administered three times per day.

* * * * *

SEQUENCE LISTING

<160> NUMBER OF SEQ ID NOS: 25

<210> SEQ ID NO 1
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 1

```
Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35
```

```
<210> SEQ ID NO 2
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 2

Lys Cys Asn Thr Ala Thr Cys Ala Thr Gln Arg Leu Ala Asn Phe Leu
1               5                  10                  15

Val Arg Ser Ser Asn Asn Phe Gly Pro Ile Leu Pro Pro Thr Asn Val
            20                  25                  30

Gly Ser Asn Thr Tyr
        35

<210> SEQ ID NO 3
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 3

Lys Cys Asn Thr Ala Thr Cys Ala Thr Gln Arg Leu Ala Asn Phe Leu
1               5                  10                  15

Val Arg Ser Ser Asn Asn Phe Gly Pro Ile Leu Pro Ser Thr Asn Val
            20                  25                  30

Gly Ser Asn Thr Tyr
        35

<210> SEQ ID NO 4
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 4

Lys Cys Asn Thr Ala Thr Cys Ala Thr Gln Arg Leu Ala Asn Phe Leu
1               5                  10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 5
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 5

Lys Cys Asn Thr Ala Thr Cys Ala Thr Gln Arg Leu Ala Asn Phe Leu
1               5                  10                  15

Val His Ser Ser Asn Asn Phe Gly Pro Val Leu Pro Pro Thr Asn Val
            20                  25                  30

Gly Ser Asn Thr Tyr
        35

<210> SEQ ID NO 6
<211> LENGTH: 37
<212> TYPE: PRT
<213> ORGANISM: Artificial Sequence
```

<220> FEATURE:
<223> OTHER INFORMATION: Synthetic peptide construct
<220> FEATURE:
<221> NAME/KEY: misc_feature
<223> OTHER INFORMATION: 2,7-Cyclo bridge

<400> SEQUENCE: 6

Lys Asp Asn Thr Ala Thr Lys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 7
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 7

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 8
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 8

Ala Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 9
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 9

Ser Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 10
<211> LENGTH: 37
<212> TYPE: PRT
<213> ORGANISM: Artificial Sequence

```
<220> FEATURE:
<223> OTHER INFORMATION: Synthetic peptide construct

<400> SEQUENCE: 10

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Pro Thr Asn Val
            20                  25                  30

Gly Ser Asn Thr Tyr
        35

<210> SEQ ID NO 11
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 11

Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Ser Thr Asn Val
            20                  25                  30

Gly Ser Asn Thr Tyr
        35

<210> SEQ ID NO 12
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 12

Cys Asn Thr Ala Thr Cys Ala Thr Gln Arg Leu Ala Asn Phe Leu Val
 1               5                  10                  15

His Ser Ser Asn Asn Phe Gly Pro Ile Leu Pro Ser Thr Asn Val Gly
            20                  25                  30

Ser Asn Thr Tyr
        35

<210> SEQ ID NO 13
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 13

Cys Asn Thr Ala Thr Cys Ala Thr Gln Arg Leu Ala Asn Phe Leu Val
 1               5                  10                  15

Arg Ser Ser Asn Asn Phe Gly Pro Ile Leu Pro Ser Thr Asn Val Gly
            20                  25                  30

Ser Asn Thr Tyr
        35

<210> SEQ ID NO 14
<211> LENGTH: 36
<212> TYPE: PRT
<213> ORGANISM: Artificial Sequence
<220> FEATURE:
<223> OTHER INFORMATION: Synthetic peptide construct
```

```
<400> SEQUENCE: 14

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Thr Asn Val Gly
            20                  25                  30

Ser Asn Thr Tyr
        35

<210> SEQ ID NO 15
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 15

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 16
<211> LENGTH: 30
<212> TYPE: PRT
<213> ORGANISM: Artificial Sequence
<220> FEATURE:
<223> OTHER INFORMATION: Synthetic peptide construct

<400> SEQUENCE: 16

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30

<210> SEQ ID NO 17
<211> LENGTH: 37
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<223> OTHER INFORMATION: c-term may be amino, alkylamino, dialkylamino,
      cycloalkylamino, arylamino, aralkylamino, alkyloxy, aryloxy, or
      aralkyloxy
<220> FEATURE:
<221> NAME/KEY: MISC_FEATURE
<222> LOCATION: (1)..(1)
<223> OTHER INFORMATION: Lys, Ala, Ser, or not present
<220> FEATURE:
<221> NAME/KEY: MISC_FEATURE
<222> LOCATION: (2)..(2)
<223> OTHER INFORMATION: Variable amino acid
<220> FEATURE:
<221> NAME/KEY: MISC_FEATURE
<222> LOCATION: (7)..(7)
<223> OTHER INFORMATION: Variable amino acid
<220> FEATURE:
<221> NAME/KEY: MISC_FEATURE
<222> LOCATION: (13)..(13)
<223> OTHER INFORMATION: Ala, Ser, or Thr
<220> FEATURE:
<221> NAME/KEY: MISC_FEATURE
<222> LOCATION: (17)..(17)
<223> OTHER INFORMATION: Val, Leu, or Ile
```

```
<220> FEATURE:
<221> NAME/KEY: MISC_FEATURE
<222> LOCATION: (18)..(18)
<223> OTHER INFORMATION: His or Arg
<220> FEATURE:
<221> NAME/KEY: MISC_FEATURE
<222> LOCATION: (19)..(19)
<223> OTHER INFORMATION: Ser or Thr
<220> FEATURE:
<221> NAME/KEY: MISC_FEATURE
<222> LOCATION: (20)..(20)
<223> OTHER INFORMATION: Ser, Thr, Gln, or Asn
<220> FEATURE:
<221> NAME/KEY: MISC_FEATURE
<222> LOCATION: (21)..(21)
<223> OTHER INFORMATION: Asn, Gln, or His
<220> FEATURE:
<221> NAME/KEY: MISC_FEATURE
<222> LOCATION: (23)..(23)
<223> OTHER INFORMATION: Phe, Leu, or Tyr
<220> FEATURE:
<221> NAME/KEY: MISC_FEATURE
<222> LOCATION: (26)..(26)
<223> OTHER INFORMATION: Ile, Val, Ala, or Leu
<220> FEATURE:
<221> NAME/KEY: MISC_FEATURE
<222> LOCATION: (29)..(29)
<223> OTHER INFORMATION: Ser, Pro, or Thr
<220> FEATURE:
<221> NAME/KEY: MISC_FEATURE
<222> LOCATION: (31)..(31)
<223> OTHER INFORMATION: Asn, Asp, or Gln

<400> SEQUENCE: 17

Xaa Xaa Asn Thr Ala Thr Xaa Ala Thr Gln Arg Leu Xaa Asn Phe Leu
 1               5                  10                  15

Xaa Xaa Xaa Xaa Xaa Asn Xaa Gly Pro Xaa Leu Pro Xaa Thr Xaa Val
                20                  25                  30

Gly Ser Asn Thr Tyr
                35

<210> SEQ ID NO 18
<211> LENGTH: 37
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<223> OTHER INFORMATION: c-term may be amino, alkylamino, dialkylamino,
      cycloalkylamino, arylamino, aralkylamino, alkyloxy, aryloxy, or
      aralkyloxy
<220> FEATURE:
<221> NAME/KEY: MISC_FEATURE
<222> LOCATION: (1)..(1)
<223> OTHER INFORMATION: Lys, Ala, Ser, or not present
<220> FEATURE:
<221> NAME/KEY: MISC_FEATURE
<222> LOCATION: (2)..(2)
<223> OTHER INFORMATION: Variable amino acid
<220> FEATURE:
<221> NAME/KEY: MISC_FEATURE
<222> LOCATION: (7)..(7)
<223> OTHER INFORMATION: Variable amino acid
<220> FEATURE:
<221> NAME/KEY: MISC_FEATURE
<222> LOCATION: (13)..(13)
<223> OTHER INFORMATION: Ala, Ser, or Thr
<220> FEATURE:
<221> NAME/KEY: MISC_FEATURE
<222> LOCATION: (17)..(17)
<223> OTHER INFORMATION: Val, Leu, or Ile
<220> FEATURE:
<221> NAME/KEY: MISC_FEATURE
<222> LOCATION: (18)..(18)
<223> OTHER INFORMATION: His or Arg
```

```
<220> FEATURE:
<221> NAME/KEY: MISC_FEATURE
<222> LOCATION: (19)..(19)
<223> OTHER INFORMATION: Ser or Thr
<220> FEATURE:
<221> NAME/KEY: MISC_FEATURE
<222> LOCATION: (20)..(20)
<223> OTHER INFORMATION: Ser, Thr, Gln, or Asn
<220> FEATURE:
<221> NAME/KEY: MISC_FEATURE
<222> LOCATION: (21)..(21)
<223> OTHER INFORMATION: Asn, Gln, or His
<220> FEATURE:
<221> NAME/KEY: MISC_FEATURE
<222> LOCATION: (23)..(23)
<223> OTHER INFORMATION: Phe, Leu, or Tyr
<220> FEATURE:
<221> NAME/KEY: MISC_FEATURE
<222> LOCATION: (26)..(26)
<223> OTHER INFORMATION: Ile, Val, Ala, or Leu
<220> FEATURE:
<221> NAME/KEY: MISC_FEATURE
<222> LOCATION: (28)..(28)
<223> OTHER INFORMATION: Ser, Pro, Leu, Ile or Thr
<220> FEATURE:
<221> NAME/KEY: MISC_FEATURE
<222> LOCATION: (31)..(31)
<223> OTHER INFORMATION: Asn, Asp, or Gln

<400> SEQUENCE: 18

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Pro Xaa Leu Xaa Pro Thr Xaa Val
            20                  25                  30

Gly Ser Asn Thr Tyr
        35

<210> SEQ ID NO 19
<211> LENGTH: 37
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<223> OTHER INFORMATION: c-term may be amino, alkylamino, dialkylamino,
      cycloalkylamino, arylamino, aralkylamino, alkyloxy, aryloxy, or
      aralkyloxy
<220> FEATURE:
<221> NAME/KEY: MISC_FEATURE
<222> LOCATION: (1)..(1)
<223> OTHER INFORMATION: Lys, Ala, Ser, or not present
<220> FEATURE:
<221> NAME/KEY: MISC_FEATURE
<222> LOCATION: (2)..(2)
<223> OTHER INFORMATION: Variable amino acid
<220> FEATURE:
<221> NAME/KEY: MISC_FEATURE
<222> LOCATION: (7)..(7)
<223> OTHER INFORMATION: Variable amino acid
<220> FEATURE:
<221> NAME/KEY: MISC_FEATURE
<222> LOCATION: (13)..(13)
<223> OTHER INFORMATION: Ala, Ser, or Thr
<220> FEATURE:
<221> NAME/KEY: MISC_FEATURE
<222> LOCATION: (17)..(17)
<223> OTHER INFORMATION: Val, Leu, or Ile
<220> FEATURE:
<221> NAME/KEY: MISC_FEATURE
<222> LOCATION: (18)..(18)
<223> OTHER INFORMATION: His or Arg
<220> FEATURE:
<221> NAME/KEY: MISC_FEATURE
<222> LOCATION: (19)..(19)
<223> OTHER INFORMATION: Ser or Thr
```

```
<220> FEATURE:
<221> NAME/KEY: MISC_FEATURE
<222> LOCATION: (20)..(20)
<223> OTHER INFORMATION: Ser, Thr, Gln, or Asn
<220> FEATURE:
<221> NAME/KEY: MISC_FEATURE
<222> LOCATION: (21)..(21)
<223> OTHER INFORMATION: Asn, Gln, or His
<220> FEATURE:
<221> NAME/KEY: MISC_FEATURE
<222> LOCATION: (23)..(23)
<223> OTHER INFORMATION: Phe, Leu, or Tyr
<220> FEATURE:
<221> NAME/KEY: MISC_FEATURE
<222> LOCATION: (25)..(25)
<223> OTHER INFORMATION: Ala or Pro
<220> FEATURE:
<221> NAME/KEY: MISC_FEATURE
<222> LOCATION: (26)..(26)
<223> OTHER INFORMATION: Ile, Val, Ala, or Leu
<220> FEATURE:
<221> NAME/KEY: MISC_FEATURE
<222> LOCATION: (31)..(31)
<223> OTHER INFORMATION: Asn, Asp, or Gln

<400> SEQUENCE: 19

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Pro Pro Thr Xaa Val
            20                  25                  30

Gly Ser Asn Thr Tyr
        35

<210> SEQ ID NO 20
<211> LENGTH: 37
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<223> OTHER INFORMATION: c-term may be amino, alkylamino, dialkylamino,
      cycloalkylamino, arylamino, aralkylamino, alkyloxy, aryloxy, or
      aralkyloxy
<220> FEATURE:
<221> NAME/KEY: MISC_FEATURE
<222> LOCATION: (1)..(1)
<223> OTHER INFORMATION: Lys, Ala, Ser, or not present
<220> FEATURE:
<221> NAME/KEY: MISC_FEATURE
<222> LOCATION: (2)..(2)
<223> OTHER INFORMATION: Variable amino acid
<220> FEATURE:
<221> NAME/KEY: MISC_FEATURE
<222> LOCATION: (7)..(7)
<223> OTHER INFORMATION: Variable amino acid
<220> FEATURE:
<221> NAME/KEY: MISC_FEATURE
<222> LOCATION: (13)..(13)
<223> OTHER INFORMATION: Ala, Ser, or Thr
<220> FEATURE:
<221> NAME/KEY: MISC_FEATURE
<222> LOCATION: (17)..(17)
<223> OTHER INFORMATION: Val, Leu, or Ile
<220> FEATURE:
<221> NAME/KEY: MISC_FEATURE
<222> LOCATION: (18)..(18)
<223> OTHER INFORMATION: His or Arg
<220> FEATURE:
<221> NAME/KEY: MISC_FEATURE
<222> LOCATION: (19)..(19)
<223> OTHER INFORMATION: Ser or Thr
<220> FEATURE:
<221> NAME/KEY: MISC_FEATURE
<222> LOCATION: (20)..(20)
<223> OTHER INFORMATION: Ser, Thr, Gln, or Asn
```

```
<220> FEATURE:
<221> NAME/KEY: MISC_FEATURE
<222> LOCATION: (21)..(21)
<223> OTHER INFORMATION: Asn, Gln, or His
<220> FEATURE:
<221> NAME/KEY: MISC_FEATURE
<222> LOCATION: (23)..(23)
<223> OTHER INFORMATION: Phe, Leu, or Tyr
<220> FEATURE:
<221> NAME/KEY: MISC_FEATURE
<222> LOCATION: (26)..(26)
<223> OTHER INFORMATION: Ile, Val, Ala, or Leu
<220> FEATURE:
<221> NAME/KEY: MISC_FEATURE
<222> LOCATION: (31)..(31)
<223> OTHER INFORMATION: Asn, Asp, or Gln

<400> SEQUENCE: 20

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Pro Xaa Leu Pro Pro Thr Xaa Val
            20                  25                  30

Gly Ser Asn Thr Tyr
        35

<210> SEQ ID NO 21
<211> LENGTH: 37
<212> TYPE: PRT
<213> ORGANISM: Rattus norvegicus
<220> FEATURE:
<221> NAME/KEY: misc_feature
<223> OTHER INFORMATION: 2,7-Cylco bridge

<400> SEQUENCE: 21

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 22
<211> LENGTH: 37
<212> TYPE: PRT
<213> ORGANISM: Homo sapiens

<400> SEQUENCE: 22

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 23
<211> LENGTH: 37
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<223> OTHER INFORMATION: c-term may be hydroxy, amino, alkylamino,
      dialkylamino, cycloalkylamino, arylamino, aralkylamino, alkyloxy,
      aryloxy, or aralkyloxy
```

```
<220> FEATURE:
<221> NAME/KEY: MISC_FEATURE
<222> LOCATION: (1)..(1)
<223> OTHER INFORMATION: Lys, Ser, Ala, acetylated Lys, or not present
<220> FEATURE:
<221> NAME/KEY: MISC_FEATURE
<222> LOCATION: (2)..(2)
<223> OTHER INFORMATION: Variable amino acid
<220> FEATURE:
<221> NAME/KEY: MISC_FEATURE
<222> LOCATION: (7)..(7)
<223> OTHER INFORMATION: Variable amino acid
<220> FEATURE:
<221> NAME/KEY: MISC_FEATURE
<222> LOCATION: (13)..(13)
<223> OTHER INFORMATION: Ala, Ser, or Thr
<220> FEATURE:
<221> NAME/KEY: MISC_FEATURE
<222> LOCATION: (17)..(17)
<223> OTHER INFORMATION: Val, Leu, or Ile
<220> FEATURE:
<221> NAME/KEY: MISC_FEATURE
<222> LOCATION: (18)..(18)
<223> OTHER INFORMATION: His or Arg
<220> FEATURE:
<221> NAME/KEY: MISC_FEATURE
<222> LOCATION: (19)..(19)
<223> OTHER INFORMATION: Ser or Thr
<220> FEATURE:
<221> NAME/KEY: MISC_FEATURE
<222> LOCATION: (20)..(20)
<223> OTHER INFORMATION: Ser, Thr, Gln, or Asn
<220> FEATURE:
<221> NAME/KEY: MISC_FEATURE
<222> LOCATION: (21)..(21)
<223> OTHER INFORMATION: Asn, Gln, or His
<220> FEATURE:
<221> NAME/KEY: MISC_FEATURE
<222> LOCATION: (23)..(23)
<223> OTHER INFORMATION: Phe, Leu, or Tyr
<220> FEATURE:
<221> NAME/KEY: MISC_FEATURE
<222> LOCATION: (25)..(25)
<223> OTHER INFORMATION: Ala or Pro
<220> FEATURE:
<221> NAME/KEY: MISC_FEATURE
<222> LOCATION: (26)..(26)
<223> OTHER INFORMATION: Ile, Val, Ala, or Leu
<220> FEATURE:
<221> NAME/KEY: MISC_FEATURE
<222> LOCATION: (28)..(28)
<223> OTHER INFORMATION: Ser, Pro, Leu, Ile, or Thr
<220> FEATURE:
<221> NAME/KEY: MISC_FEATURE
<222> LOCATION: (29)..(29)
<223> OTHER INFORMATION: Ser, Pro, or Thr
<220> FEATURE:
<221> NAME/KEY: MISC_FEATURE
<222> LOCATION: (31)..(31)
<223> OTHER INFORMATION: Asn, Asp, or Gln

<400> SEQUENCE: 23

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr
        35

<210> SEQ ID NO 24
<211> LENGTH: 37
<212> TYPE: PRT
<213> ORGANISM: Artificial Sequence
<220> FEATURE:
<223> OTHER INFORMATION: Synthetic peptide construct
```

```
<220> FEATURE:
<221> NAME/KEY: MISC_FEATURE
<222> LOCATION: (11)..(11)
<223> OTHER INFORMATION: Arg is a D amino acid residue

<400> SEQUENCE: 24

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 25
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 25

Cys Asn Thr Ala Thr Cys Ala Thr Gln Arg Leu Ala Asn Phe Leu Val
1               5                   10                  15

His Ser Ser Asn Asn Phe Gly Pro Val Leu Pro Pro Thr Asn Val Gly
            20                  25                  30

Ser Asn Thr Tyr
        35
```